(12) United States Patent
Yarnitsky et al.

(10) Patent No.: US 6,287,324 B1
(45) Date of Patent: Sep. 11, 2001

(54) SELF-DRILLING SURGICAL SUTURE ANCHOR

(75) Inventors: Yeshayahu Yarnitsky, Haifa; Gordon Edelson; Shay Kahana, both of D.N. Emek Hayarden, all of (IL)

(73) Assignee: Shoulderon Ltd., Zemach (IL)

( * ) Notice: Subject to any disclaimer, the term of this patent is extended or adjusted under 35 U.S.C. 154(b) by 0 days.

(21) Appl. No.: 09/493,685

(22) Filed: Jan. 28, 2000

(51) Int. Cl.[7] ................................................. A61B 17/04
(52) U.S. Cl. .............................................................. 606/232
(58) Field of Search ................................ 606/72–73, 148, 606/150, 232–233, 65; 623/11

(56) References Cited

U.S. PATENT DOCUMENTS

| | | | | |
|---|---|---|---|---|
| 5,037,422 | * | 8/1991 | Hayhurst et al. | 606/72 |
| 5,268,001 | * | 12/1993 | Nicholson et al. | 606/72 |
| 5,527,342 | * | 6/1996 | Pietrzak et al. | 606/232 |
| 5,571,139 | * | 11/1996 | Jenkins, Jr. | 606/232 |
| 5,584,836 | * | 12/1996 | Ballintyn et al. | 606/73 |
| 5,618,314 | * | 4/1997 | Harwin et al. | 606/232 |
| 5,665,111 | * | 9/1997 | Ray et al. | 606/232 |
| 5,702,448 | * | 12/1997 | Buechel et al. | 606/65 |
| 5,824,079 | * | 10/1998 | Siegler et al. | 623/11 |
| 5,849,004 | * | 12/1998 | Bramlet | 606/232 |

* cited by examiner

Primary Examiner—Cary E. O'Connor
(74) Attorney, Agent, or Firm—Mark M. Friedman

(57) ABSTRACT

A device and method for anchoring a surgical suture in solid tissue, such as bone, which is implantable without prior drilling of a hole. The device for anchoring a surgical suture to a solid tissue is attachable to an external rotational drive and includes a self-drilling body to which surgical suture is attachable, an assembly including at least one flexible locking element, attached to or integrally formed therewith, capable of assuming both an open and closed configurations. The device is configured so that the assembly including at least one flexible locking element in the closed configuration is releasably engageable by the external rotational drive. The method for anchoring a surgical suture to a solid tissue includes the step of causing a self-drilling body to penetrate a soft tissue, the step of aligning the self-drilling body with an anchor point on a bone, the step of activating an external rotational drive, thereby causing the self-drilling body to rotate and penetrate the anchor point in the bone, and the step of actuating a mechanism for anchoring the self-drilling body in the bone at the anchor point.

19 Claims, 4 Drawing Sheets

SELF-DRILLING SURGICAL SUTURE ANCHOR

FIELD AND BACKGROUND OF THE INVENTION

The present invention relates to a surgical suture anchor for implantation in solid tissue, such as bone, which is implantable without prior drilling of a hole in the solid tissue. More particularly, the present invention relates to a surgical anchor which can both pierce soft tissue, such as muscle, and drill into bone. The surgical anchor is self-setting within the solid tissue and serves as a point of attachment for suture material which serves to attach a soft tissue to the solid tissue containing the implanted anchor.

In orthopedic surgery there is often a need to attach a soft tissue, including but not limited to muscle, to a solid tissue, including but not limited to bone. A number of prior art devices, referred to collectively as suture anchors, exist to perform this function.

Suture anchors for anchoring a suture to solid tissue, such as bone, so that a soft tissue, such as muscle or ligament, may be sutured to the bone are known in the art. Such suture anchors come in a variety of shapes and designs which are reviewed in James E. Carpenter et al., "Pull-Out Strength of Five Suture Anchors", Arthroscopy, 9(1), pp. 109–113 (1993). These suture anchors may be divided into several categories.

The first category is the harpoon-type or screw-type suture anchor, which are drilled into cortical bone. This type is represented by, for example, Cerrier et al. U.S. Pat. No: 5,100,417 and Hayhurst et al. Canada PAT. NO: 2,045,903. This type of suture anchor is held in place by a variety of methods including self-tapping, force fitting, and inclusion of a resilient portion which flexes to frictionally engage the bone material.

An additional category of suture anchor includes a rigid member and a flexible, shape memory member. The flexible member lies flat against the rigid member during insertion, and flexes away from the rigid member once lodged inside the bone. This category includes, for example, the prior art teachings of Gatturna et al. U.S. Pat. Nos: 5,046,513 and 5,192,303.

A third category of suture anchor is substantially elongated and is inserted with its longitudinal axis substantially parallel to the bone hole through which it is inserted. The orientation of the suture anchor is then adjusted upon reaching cancellous bone tissue by pulling on the attached suture. This category of anchor is exemplified by Hayhurst et al. U.S. Pat. No: 5,041,129 and Noblitt et al. U.S. Pat. No: 5,203,787.

According to the teachings of Hayhurst, the suture anchor has a substantially cylindrical rigid body with a central cavity and a longitudinal slot extending from one end to approximately the middle of the rigid body. A suture is positioned inside the central cavity, and the anchor is inserted with the slot entering the bone last. After properly positioning the anchor, the suture is pulled through the slot towards its base, thereby reorienting the anchor with respect to the bone, thereby fixing it in place.

According to the teachings of Noblitt, the suture anchor has an offset portion to facilitate attachment of a suture. Once the anchor has been placed in cancellous tissue, the suture is pulled in such a way that it reorients the anchor so that its longitudinal axis is substantially transverse to the bone hole through which it was inserted.

A disadvantage common to all members of this third category of anchors is that tension on the suture required for reorientation of the anchor may put undue stress on the suture. In addition, the introduction technique is complicated, requiring multiple insertion tools.

All of the above-described suture anchors typically require complex insertion tools, the use of which is time consuming and requires considerable skill. Insertion of these prior art devices often requires pre-drilling of the bone (U.S. Pat. Nos.: 4,898,156; 4,899,743; 4,946,468; 4,968,315; 5,002,550; 5,501,695; 5,540,718). Pre-drilling is disadvantageous because it requires positioning of a soft tissue relative to a solid tissue, selection of a site for drilling, release of the soft tissue, drilling into the solid tissue, insertion of the anchor, and repositioning of the soft tissue. This process is time consuming and difficult. Repositioning of the soft tissue after drilling may be inexact, leading to sub-optimal attachment. The process lengthens the time of surgery increasing patient anxiety and distress.

A fourth category of anchors includes screws which are either self-tapping (for example U.S. Pat. No: 4,632,100) or require drilling of a pilot hole. Screws often loosen with time, necessitating a second operation to remove the loosened screw. In addition, when screws are set in bone, the heads of the screws can protrude above the surface of the bone in which they are set. These exposed screw heads present an abrasive surface to surrounding soft tissue which may cause inflammation or tissue damage. If a pilot hole must be drilled into the bone, the installation procedure becomes lengthy, more so if the pilot hole must be tapped to accept the screw. In addition, the nature of a screw attachment tends to require that the pilot hole be located on a relatively flat section of the bone, and toothed washers must frequently be used in conjunction with the screws to fasten the desired objects to the target bone. As a result of these constraints, it may be necessary to locate the attachment point at a less than optimal position.

A fifth category of anchors includes staples which are tapped or hammered into the bone. Staples have their own set of disadvantages. Bone staples must frequently be removed after they have been in position for some time, necessitating a second operation. In addition, staples must be positioned so as to maximize their holding power in the bone and such positioning may conflict with the otherwise-optimal position for attachment of objects to bone. The most serious drawback of staples is that they may crack the bone during deployment, or accidentally transect the object (e.g. soft tissue) being attached to the bone, since it is difficult to control the extent of the staple's penetration into the bone. Finally, once the staple has been set into the bone, it is impossible to adjust the degree of tension being applied to the object which is being attached to the bone without setting a new staple.

In addition, prior art anchors which require drilling of holes in the bone typically require holes with a diameter between 2.4 and 3.7 mm (radius (r) of 1.2 to 1.85 mm). Since weakening of the bone is proportional to the area of the hole drilled, and since the area (a) increases according to the formula $a=\pi(r^2)$ a small reduction in the diameter of the hole will greatly reduce the area of the hole and therefore greatly reduce the degree to which the structural integrity of the bone is compromised. For example, a prior art device requiring a hole with a diameter of 2.4 mm has an area of 4.52 mm$^2$. Reducing the diameter of the hole to 1.8 mm, a 25% reduction, reduces the area to 2.54 mm$^2$, a reduction of 44%. Therefore, any invention which reduces the size of the hole in the bone required to implant an anchor is inherently advantageous because it facilitates retention of more of the structural integrity of the bone.

The prior art teaches coating of materials to be implanted within the body with bio-resorbable polymers such as poly (alpha-hydroxy-carboxylic acid)/poly (oxyalkylene) to reduce inflammation and adhesions after surgical implantation of a foreign body within a patient. (for example U.S. Pat. Nos: 4,826,945 and 5,711,958). This material, or other bio-resorbable polymers, may be used in conjunction with implantable surgical anchors.

Citation or identification of any reference in this section or in any other section of this application shall not be construed as an admission that such reference is available as prior art to the present invention.

There is thus a widely recognized need for, and it would be highly advantageous to have, a surgical suture anchor which does not require pre drilling of a hole, which is unthreaded, which can be installed without benefit of special tools, which concurrently pierces soft tissue and bone, and which makes a narrower diameter hole in the bone than existing alternatives.

SUMMARY OF THE INVENTION

According to one aspect of the present invention there is provided a device for anchoring a surgical suture to a solid tissue being attachable to an external rotational drive, the device comprising: (a) a self-drilling body having a point of attachment for surgical suture, the self-drilling body capable of penetrating both soft tissue and solid tissue, and the body having an effective drilling diameter; (b) an assembly including at least one flexible locking element, capable of assuming both an open configuration wider than the effective drilling diameter and a closed configuration at least as narrow as the effective drilling diameter, the at least one flexible locking element being attached to or integrally formed with said self-drilling body; and (c) an overall configuration in which the assembly including at least one flexible locking element in said closed configuration is releasably engageable by the external rotational drive According to another aspect of the present invention there is provided a method for anchoring a surgical suture to a solid tissue, the method comprising the steps of: (a) causing a self-drilling body to penetrate a soft tissue; (b) aligning the self-drilling body with a desired anchor point on a bone; (c) activating an external rotational drive, thereby causing the self-drilling body to rotate and penetrate the desired anchor point in the bone; and (d) actuating a mechanism for anchoring the self-drilling body in the bone at the anchor point.

According to further features in preferred embodiments of the invention described below, surgical suture is attached to the point of attachment for surgical suture prior to placement of the anchor in bone.

According to still further features in the described preferred embodiments, the point of attachment for surgical suture rotates freely with respect to the self-drilling body.

According to still further features in the described preferred embodiments there is provided a low friction coating on said self-drilling body, said coating configured to prevent damage to a soft tissue as the body penetrates the soft tissue.

According to further features in preferred embodiments of the invention described below, the low friction coating is selected from the group of bio-resorbable polymers consisting of polyethers, poly alpha-hydroxy acids, and combinations thereof.

According to still further features in the described preferred embodiments the self-drilling body is composed of a metal selected from the group of metals consisting of stainless steel, gold, titanium, nickel, aluminum and alloys thereof.

According to further features in preferred embodiments of the invention described below, the assembly including at least one flexible locking element automatically assumes an open configuration substantially wider than the effective drilling diameter when the external rotational drive is detached after drilling, thereby anchoring the device in the bone.

According to still further features in additional preferred embodiments, the assembly including at least one flexible locking element assumes an open configuration substantially wider than the effective drilling diameter as a result of a mechanical force applied to the device, thereby anchoring the device in said bone.

According to yet another aspect of the present invention there is provided a method for preserving the inherent integrity of a bone during implantation of a surgical suture anchor, the method comprising the step of creating a hole in the bone, the hole having a diameter of less than about 2.0 mm.

According to further features in preferred embodiments of the invention described below, the diameter of the hole is no more than about 1.6 mm.

According to still further features in the described preferred embodiments, the diameter of the hole is no more than about 1.4 mm.

According to still further features in the described preferred embodiments, the diameter of the hole is no more than about 1.0 mm.

The present invention successfully addresses the shortcomings of the presently known configurations by providing a device and method for anchoring a surgical suture in bone without pre-drilling a hole, without use of complicated installation tools, and without unduly compromising the integrity of the bone.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
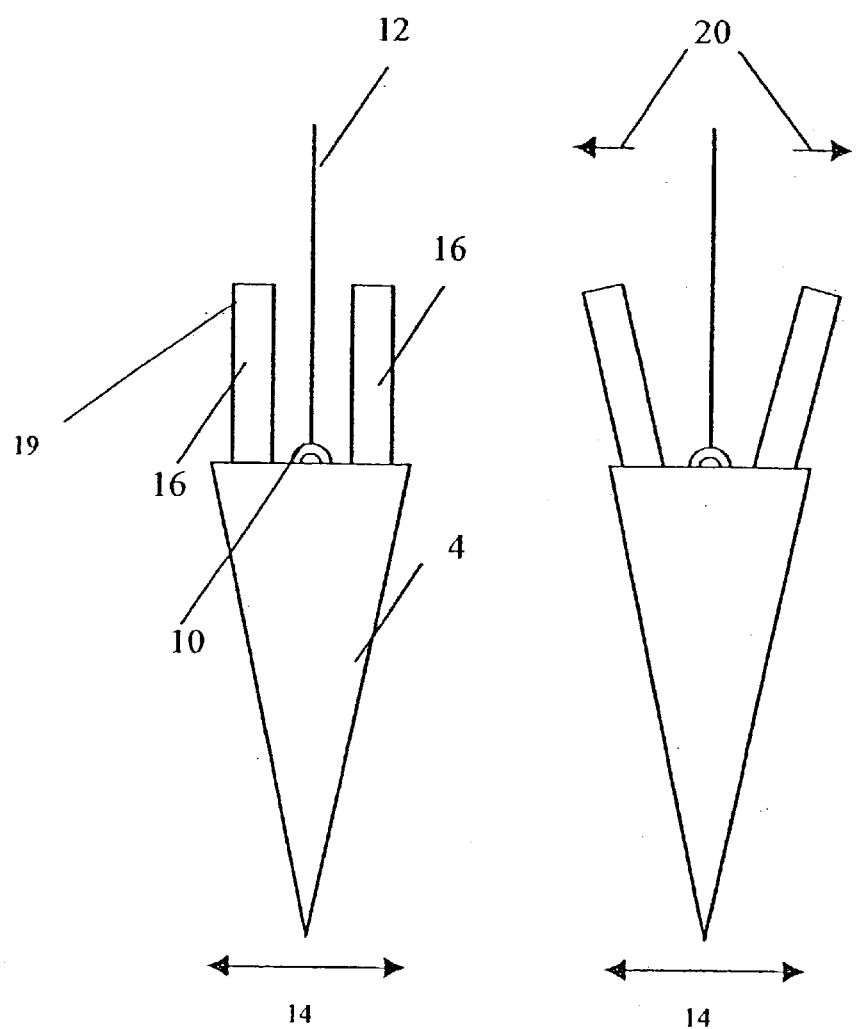
FIG. 1 is a side view a preferred embodiment of the device of the present invention showing the tendency of the device to revert from a closed configuration to an open configuration in which the width of the device is greater than the effective drilling diameter.

The present invention is of a device and method for anchoring a surgical suture to a solid tissue, including but not limited to, bone. The present invention does not require pre-drilling a hole, use of complicated installation tools, or undue compromise of the integrity of the bone. Specifically, the present invention can be used to accurately align a soft tissue with a desired anchor point and attach the soft tissue to the desired anchor point.

The principles and operation of a device and method for anchoring a surgical suture to a solid tissue according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of this specification and the accompanying claims, the term "self-drilling body" refers to any body which is rotationally insertable into a surface without prior drilling of a hole in that surface.

For purposes of this specification and the accompanying claims, the term "point of attachment for surgical suture" refers to a portion of the self-drilling body which is designed to hold the suture material securely to the self-drilling body under the conditions of use described herein.

For purposes of this specification and the accompanying claims, the term "anchor point" refers to a location in a solid tissue chosen by the person deploying the device of the present invention, the anchor point being the position at which the self-drilling body will be inserted into the solid tissue.

For purposes of this specification and the accompanying claims, the term "widest point", as used with respect to the self-drilling body, refers to the point at which the body has the greatest diameter in a plane perpendicular to a vertical axis of the body.

Referring now to the drawings, FIG. 1 illustrates the device of the present invention in open 2 and closed 3 configurations. The device comprises: (a) self-drilling body 4 having a point of attachment for surgical suture 10, self-drilling body 4 being capable of penetrating both soft tissue and bone, and having an effective drilling diameter 14 represented in the drawing by a double headed arrow; (b) an assembly including at least one flexible locking element 16 (two are pictured), capable of assuming both an open configuration 3 wider than effective drilling diameter 14 and a closed configuration 2 at least as narrow as effective drilling diameter 14, wherein flexible locking elements 16 are attached to or integrally formed with self-drilling body 4; and (c) an overall configuration in which the assembly including at least one flexible locking element 16 in closed configuration 2 is releasably engageable by the external rotational drive(not pictured).

Upon disassembly from the external rotational drive, the device is transformed from closed configuration 2 to open configuration 3 via outward movement of flexible locking elements 16 as indicated by arrows 20. This transformation is automatic in the pictured preferred embodiment of the present invention because of an inherent spring-like memory in locking elements 16. Alternate preferred embodiments accomplish this transformation automatically via other means, including but not limited to the use of springs which are not integral parts of locking mechanism 16. Additional preferred embodiments feature a transformation from closed configuration 2 to open configuration 3 which is the result of a mechanical force applied to device 2 by, for example, pulling on suture 12.

According to preferred embodiments of the present invention, self-drilling body 4 may be constructed of materials including, but not limited to, at least one metal selected from the group of metals consisting of stainless steel, titanium, gold, nickel, aluminum and alloys thereof either with or without the addition of diamond pieces as a coating. According to some preferred embodiments of the present invention a low friction coating of a bio-resorbable polymer consisting of polyethers, poly alpha-hydroxy acids, or combinations thereof is added to prevent damage to soft tissue as the self-drilling body passes therethrough.

According to preferred embodiments of the present invention, suture 12 is attached to suture point of attachment 10 prior to implantation of self-drilling body 4 in a bone of a patient. However, the present invention also encompasses embodiments in which suture 12 is attached to suture point of attachment 10 after implantation of self-drilling body 4.

Figure 3:
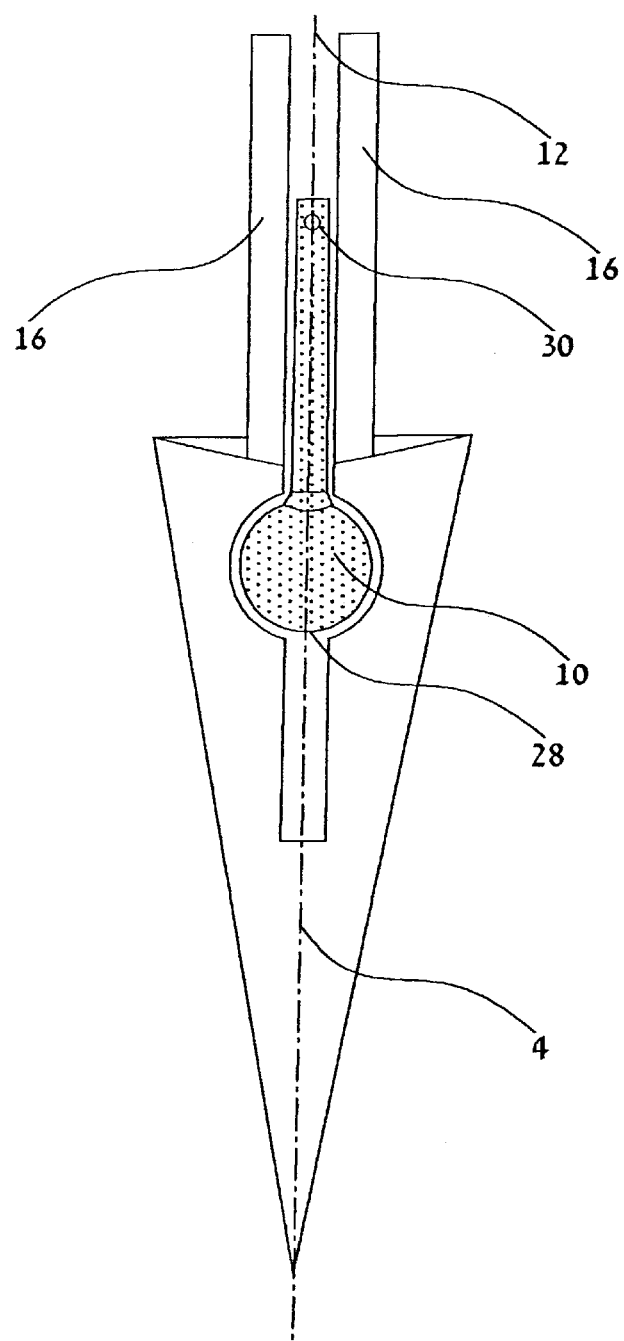
FIG. 3 is a diagram of a second preferred embodiment of the device featuring a rotating suture point of attachment.
Figure 4:
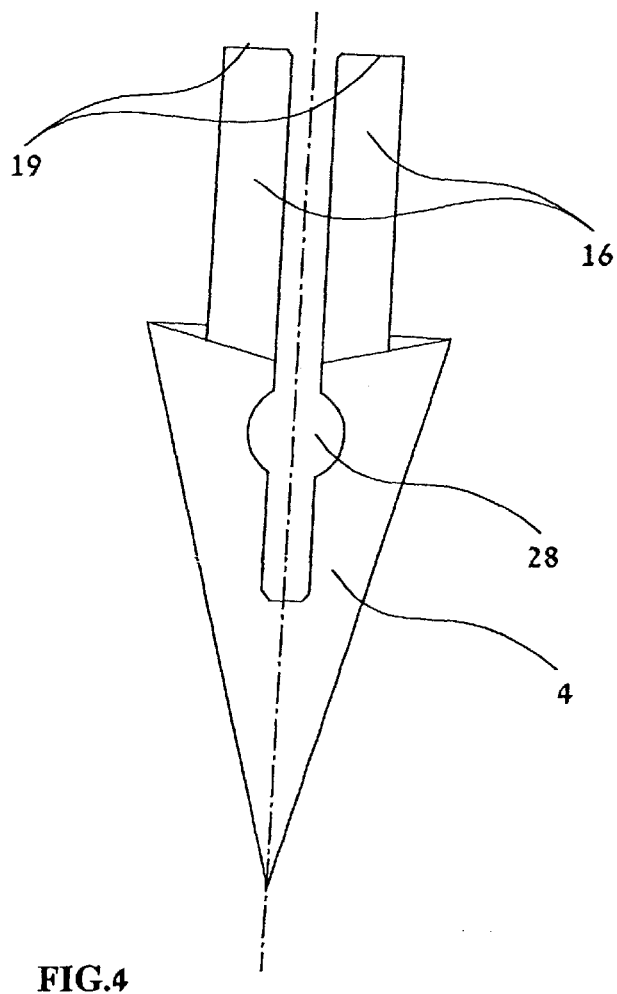
FIG. 4 is a diagram of the preferred embodiment of FIG. 3 featuring a rotating suture point of attachment with the suture point of attachment removed.
Figure 5:
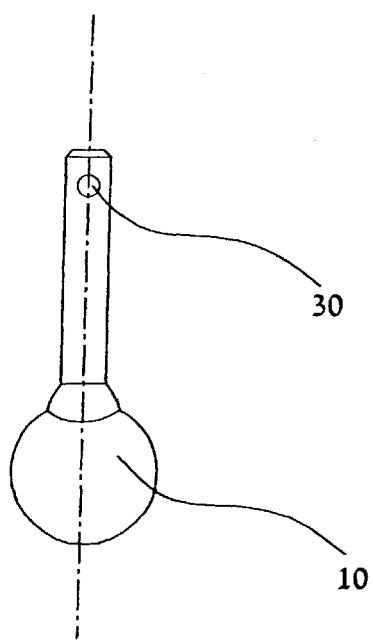
FIG. 5 is a diagram of the rotating suture point of attachment for use with the device of FIG. 3.

According to some preferred embodiments (FIGS. 3, 4 and 5), point of attachment for surgical suture 10 is situated in receptacle 28 where it rotates freely with respect to self-drilling body 4 while connected to suture material 12 by means of hole 30. According to some preferred embodiments, tension on suture material 12 attached to hole 30 causes flexible locking elements 16 to change from closed configuration 2 to open configuration 3.

In order to use the device of the present invention, it must first be attached to an external rotational drive, forcing it to assume closed configuration 2. This rotational drive is selected from commercially available rotational drives. As a result, flexible locking element 16 may assume any one of a number of configurations in order to be engageable by the chosen external rotational drive. The present invention is intended to encompass all configurations of locking elements 16 which fit existing rotational drives, as well as all configurations of locking elements 16 which may be required to be engageable by rotational drives which become available in the future.

In order to use the device of the present invention, self-drilling body 4 is forced through a soft tissue during use. In embodiments where self-drilling body 4 is rotating during this process, a low friction coating may be present upon self-drilling body 4 to prevent soft tissue damage during this step. The low friction coating is subsequently self removing as the self-drilling body begins to enter the bone. Such a coating might be composed of, for example, polyethers, poly alpha-hydroxy acids, or combinations thereof, such as Repel™ (Life Medical Sciences, Edison, N.J.).

Figure 2:
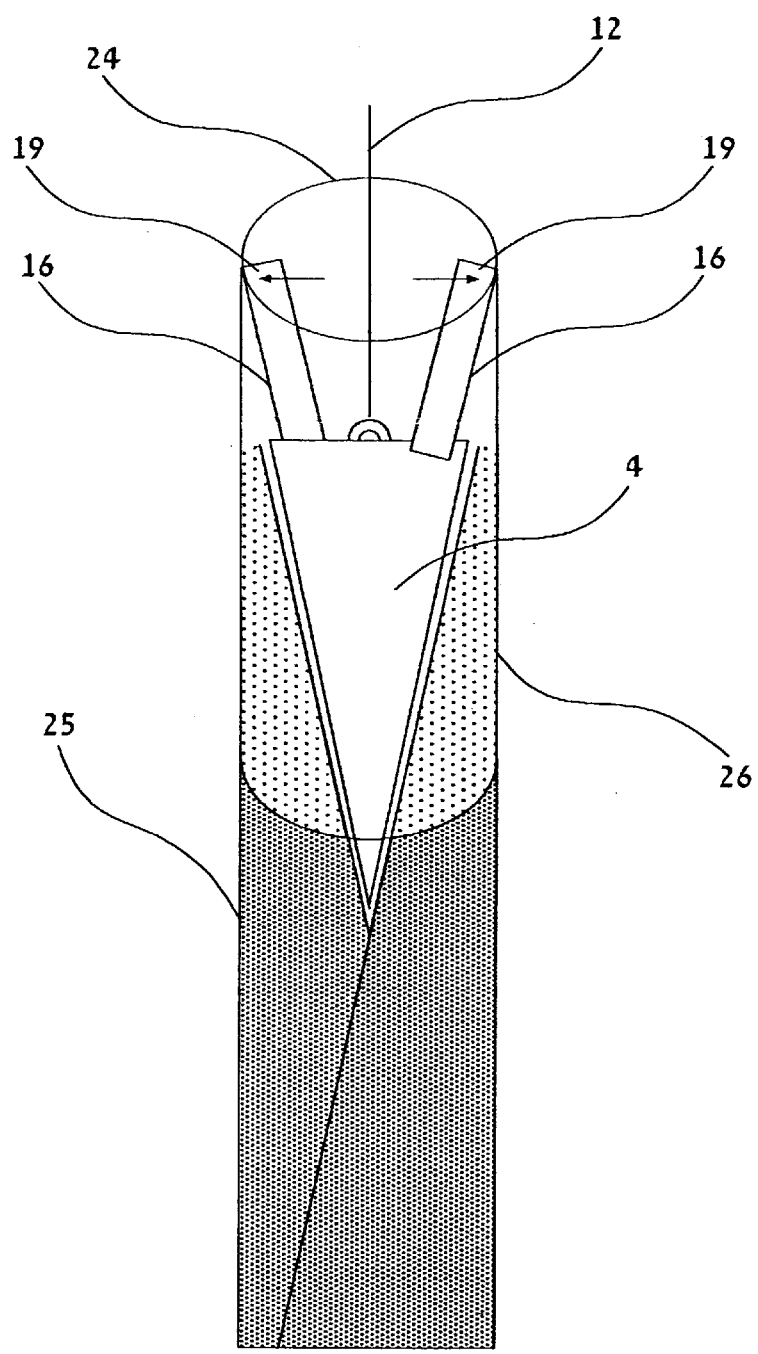
FIG. 2 is a diagram of the device anchored within a hole bored in bone.

Self-drilling body 4 is then aligned with a desired anchor point on a bone. The external rotational drive is activated, thereby causing self-drilling body 4 to rotate and create a circular hole 24 (FIG. 2) at the desired anchor point. As self-drilling body 4 penetrates the bone, a cylindrical cavity 26 is created. This cavity will conform at its deepest point to the shape of the leading edge of self-drilling body 4, forming, for example, a cone (FIG. 2) as defined by shaded area 25. After self-drilling body 4 has penetrated the bone to the desired depth, the external rotational drive is detached. According to preferred embodiments, this detachment automatically actuates a mechanism for anchoring self-drilling body 4 in the newly created cylindrical cavity 26 by means of locking mechanism 16 which assume open configuration 3, in which the distance between ends 19 of locking mechanism 16 is greater than effective drilling diameter 14. According to alternate embodiments, actuation of this anchoring mechanism requires a mechanical input, including but not limited to, application of tension to suture 12.

According to preferred embodiments of the present invention, effective drilling diameter 14 is less than about 2 mm, more preferably less than about 1.6 mm, more preferably less than about 1.4 m, most preferably less than about 1.0 mm. This feature serves to preserve bone integrity, allowing installation of numerous anchors in close proximity to one another without undue risk to the patient.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications cited herein are incorporated by reference in their entirety.

What is claimed is:

1. A device for anchoring a surgical suture to a solid tissue, the device being attachable to an external rotational drive, the device comprising:
   (a) a self-drilling body having a point of attachment for surgical suture, said self-drilling body being configured for penetrating both soft tissue and solid tissue, and said body defining an effective drilling diameter;
   (b) an assembly including at least one flexible locking element said assembly capable of assuming both an open configuration wider than said effective drilling diameter and a closed configuration at least as narrow as said effective drilling diameter, said at least one flexible locking element being attached to or integrally formed with said self-drilling body; and
   (c) the device being configured so that said assembly including at least one flexible locking element in said closed configuration is releasably engageable by the external rotational drive;
   wherein said self drilling body is rotationally insertable into a surface without prior drilling of a hole in said surface;
   wherein said assembly including at least one flexible locking element automatically assumes an open state substantially wider than said effective drilling diameter when said external rotational drive is detached after drilling, thereby anchoring said device in said solid tissue.

2. The device of claim 1, further comprising:
   (d) surgical suture attached to said point of attachment for surgical suture.

3. The device of claim 1, wherein said point of attachment for surgical suture rotates freely with respect to said self-drilling body.

4. The device of claim 1, further comprising:
   (e) a low friction coating on said self-drilling body, configured so as to prevent damage to a soft tissue as said body penetrates said soft tissue.

5. The device of claim 4, wherein said coating is selected from the group of bio-resorbable polymers consisting of polyethers and poly alpha-hydroxy acids.

6. The device of claim 4, wherein said coating is formed from a bio-resorbable polymer consisting of a combination of polyethers and poly alpha-hydroxy acids.

7. The device of claim 1, wherein said self-drilling body is composed of a metal selected from the group of metals consisting of stainless steel, titanium, gold, nickel and aluminum.

8. The device of claim 1, wherein said self-drilling body is composed of an alloy of metals selected from the group of metals consisting of stainless steel, titanium, gold, nickel and aluminum.

9. The device of claim 1, wherein said self-drilling body additionally comprises a coating of diamond pieces.

10. The device of claim 1, wherein assembly including at least one flexible locking element assumes an open state substantially wider than said effective drilling diameter as a result of a mechanical force applied to said device, thereby anchoring said device in said solid tissue.

11. A method for anchoring a surgical suture to a solid tissue, the method comprising the steps of:
   (a) causing a self-drilling body to penetrate a soft tissue;
   (b) aligning said self-drilling body with a desired anchor point on a bone;
   (c) activating an external rotational drive, thereby causing said self-drilling body to rotate and penetrate said anchor point in said bone; and
   (d) actuating a mechanism for anchoring said self-drilling body in said bone at said anchor point;
       wherein said mechanism for anchoring is actuated by detachment of said device from said external rotational drive.

12. The method of claim 11 wherein said self-drilling body comprises:
   (i) a point of attachment for surgical suture;
   (ii) a widest point which defines an effective drilling diameter;
   (iii) an assembly including at least one flexible locking element, said assembly capable of assuming both an open configuration wider than said effective drilling diameter and a closed configuration at least as narrow as said effective drilling diameter, said at least one flexible locking element being attached to or integrally formed with said self-drilling body; and
   (iv) a configuration in which said assembly including at least one flexible locking element in said closed configuration is releasably engageable by the external rotational drive.

13. The method of claim 12, wherein said point of attachment for surgical suture rotates freely with respect to said self-drilling body.

14. The method of claim 11, further comprising the step of:
   (f) coating said self-drilling body with a low friction coating, said coating configured so as to prevent damage to said soft tissue as said body penetrates said soft tissue.

15. The method of claim 14, wherein said coating is selected from the group of bio-resorbable polymers consisting of polyethers and poly alpha-hydroxy acids.

16. The method of claim 14, wherein said coating is formed from a bio-resorbable polymer consisting of a combination of polyethers and poly alpha-hydroxy acids.

17. The method of claim 11, wherein said self-drilling body is composed of a metal selected from the group of metals consisting of stainless steel, titanium, gold, nickel and aluminum.

18. The method of claim 11, wherein said self-drilling body is composed of an alloy of metals selected from the group of metals consisting of stainless steel, titanium, gold, nickel and aluminum.

19. The method of claim 11, wherein said self-drilling body additionally comprises a coating of diamond pieces.

* * * * *